United States Patent [19]

Mündnich et al.

[11] 4,336,206

[45] Jun. 22, 1982

[54] PROCESS FOR THE MANUFACTURE OF CYANOHYDRIN ACYLATES OF ALDEHYDES

[75] Inventors: Rainer Mündnich, Frankfurt am Main; Manfred Finke, Kelkheim; Walter Rupp, Königstein; Klaus Dehmer, Kelkheim, all of Fed. Rep. of Germany

[73] Assignee: Hoechst Aktiengesellschaft, Frankfurt am Main, Fed. Rep. of Germany

[21] Appl. No.: 149,969

[22] Filed: May 15, 1980

[30] Foreign Application Priority Data

May 17, 1979 [DE] Fed. Rep. of Germany ....... 2919974

[51] Int. Cl.³ .................. C07C 120/00; C07C 121/38; C07C 121/46; C07C 121/66
[52] U.S. Cl. ................................ 260/465.4; 260/464; 260/465 D
[58] Field of Search ................. 260/464, 465 D, 465.4

[56] References Cited

FOREIGN PATENT DOCUMENTS 810026 8/1951 Fed. Rep. of Germany .

OTHER PUBLICATIONS

Rambaud, *Bull. Soc. Chem.*, 1, pp. 1326–1327 (1934).
Palm, et al., *Angew. Chem.*, 78, p. 1096 (1966).
Nowak, J. Org. Chem., 28, (1963), pp. 1182–1187.
McIntosh, Can. J. Chem., 55, (1977), pp. 4200–4205.

*Primary Examiner*—Joseph Paul Brust
*Attorney, Agent, or Firm*—Curtis, Morris & Safford

[57] ABSTRACT

Cyanohydrin acylates of aldehydes are manufactured by reacting aldehydes with aqueous solutions of cyanides and organic acid chlorides or anhydrides in the molar ratio of aldehyde:cyanide:acid chloride or anhydride of 1:1:1 with deviations of at most only about 10%, optionally in the presence of an inert organic solvent immiscible with water in a one-stage process. The process products are intermediates mainly in the fields of pharmaceuticals and plant protection.

16 Claims, No Drawings

PROCESS FOR THE MANUFACTURE OF CYANOHYDRIN ACYLATES OF ALDEHYDES

Cyanohydrin acylates of aldehydes are valuable intermediates in various fields of application, especially in the fields of pharmaceuticals and plant protection.

A great number of different processes have been known for the manufacture of cyanohydrin acylates of aldehydes. The most important processes may essentially be divided into two groups, i.e., two-stage processes and one-stage processes.

In the two-stage processes, the corresponding aldehyde cyanohydrin is prepared in the first stage from the respective aldehyde and HCN or aqueous cyanide. The cyanohydrin is then converted in the second process stage into the desired aldehyde cyanohydrin acylate by reaction with an organic acid halide or anhydride.

According to a two-stage process of this kind—although it is not of recent date—it is possible to manufacture for example acrolein-cyanohydrin acetate, which may well be the best-known cyanohydrin acylate of an $\alpha,\beta$-unsaturated aldehyde [Van Sleen, Rec. Trav. CHem. P.—vol. 21, pages 209 et seq., especially p. 215 (1902l)]. The acrolein cyanohydrin obtained at first in usual manner from acrolein and HCN or aqueous cyanide is accordingly reacted with excess acetic anhydride in the presence of about 50 molar % of sodium acetate at a temperature of up to about 80° C.; on the basis of the numerical values reported, a yield of about 33% of the theory is calculated for the reaction of the acrolein cyanohydrin with the acetic anhydride.

R. Rambaud [Bull. Soc. Chim. 1, pages 1317 et seq., especially p. 1326 (1934)] states to have obtained a yield of 70% of the theory of acrolein-cyanohydrin acetate according to the same method.

However, the rather complicated work-up of the reaction mixture (cf. Van Sleen, as cited above) makes the method appear less suitable for industrial use, for it is necessary to extract the acrolein-cyanohydrin acetate with ether from the reaction mixture after degradation of the excess acetic anhydride, which may therefore not be recirculated into the process, then the organic phase obtained must be neutralized with sodium carbonate solution, dried over anhydrous sodium sulfate, filtered, concentrated, and finally further purified by vacuum distillation.

Furthermore, the acrolein-cyanohydrin acetate thus prepared has a purity of at most only about 83% (determined by way of gas chromatography), as tests have shown which were carried out by the applicants, so that Rambaud, too, can hardly have obtained more than about 58% of the theory of pure acrolein-cyanohydrin acetate. Due to the insufficient purity of the product obtained in this known process, said product cannot be used without additional purification for a series of reactions, for example radical reactions, in which already minor impurities have a strongly disturbing effect.

Another method for the manufacture of acetaldehyde cyanohydrin acetate [R. M. Nowak, J. Org. Chem. 28, pages 1182 to 1187, especially p. 1186 (1963)] starts with an aqueous NaCN (2 molar) solution, to which at first acetaldehyde (1 mol) is added slowly. At a temperature of from $-10°$ C. to 0° C., acetyl chloride (1.2 mols) or acetic anhydride is added dropwise, and the solution subsequently diluted with water is extracted with ether, the ether layer being fractionated.

The resulting yield of acetaldehyde-cyanohydrin acetate is stated to be 90% of the theory. Furthermore, special attention is drawn to the fact that for optimum yields a NaCN excess is required—in the example this excess is 100%—and that equimolar amounts of cyanide and aldehyde reduce the yield to about 55 to 65%.

An embodiment of a one-stage process for the manufacture of cyanohydrin acylates of aldehydes has been described for example by R. Palm, H. Ohse and H. Cherdron in Angew. Chem. 78, page 1093 (1966) in consequence of the manufacture of the acrolein-cyanohydrin acetate. According to this description, 0.77 mol of acetic acid anhydride was rapidly added dropwise to a cooled mixture of acrolein (0.77 mol) in benene—with practically no reaction taking place yet——and thereafter a solution of NaCN (1.12 mols) in water was added. Stirring was continued for some time with cooling to $-10°$ C., then the mixture was allowed to reach 0° C., and the batch was worked up in common manner (neutralization and drying of the organic phase prior to distillation). The resulting yield of acrolein-cyanohydrin acetate was reported to be 87% of the theory. It is a remarkable fact that also in this process there was used a considerable cyanide excess (about 45%) as compared with the amount theoretically necessary and that a relatively complicated work-up was required.

In another known one-stage process for the manufacture of cyanohydrin acylates of aldehydes, [McIntosh, Can. J. Chem. 55, pages 4200 et seq., especially p. 4204 (1977)], a smaller cyanide excess (20%) is indeed used, yet, on the other hand, a phase transfer catalyst (triethylbenzyl-ammonium chloride) is additionally added. In said process, a mixture of aldehyde and acetic anhydride in methylene chloride is added dropwise, at 0° C., to a mixture of KCN, water, methylene chloride and the phase transfer catalyst. In the case of the preparation of crotonaldehyde-cyanohydrin acetate, for example, the yield is stated to have been 66% of the theory of isolated product.

The known methods for the manufacture of cyanohydrin acylates of aldehydes are only suitable to an insufficient degree, especially for use on an industrial scale, for these methods either lead to an insufficient yield and purity of the desired product (Van Sleen, Rambaud, cf. above), or partially high excess amounts of acylating agents and especially cyanide are required (Nowak; Palm, Ohse and Cherdron, cf. above), which not only requires a complicated isolation and product purification, but also makes a considerable waste water purification necessary. Or, in cases where there has been used only a smaller cyanide excess (McIntosh, cf. above), a phase transfer catalyst must also be employed, whose separation and recovery also mean a considerable expenditure.

There has therefore been the task to find an improved process for the manufacture of cyanohydrin acylates of aldehydes which no longer exhibits the drawbacks of the known processes and which may be carried out also on an industrial scale in an efficient and economical manner.

Said task could be solved according to the invention in a simple and satisfactory manner by practically using no more excess amounts of cyanide and acid chloride or acid anhydride in the known one-stage processes.

Hence, the subject of the invention is a process for the manufacture of cyanohydrin acylates of aldehydes by reacting aldehydes with aqueous solutions of cyanides and organic acid chlorides or acid anhydrides, optionally in the presence of an inert organic solvent immiscible with water, in a one-stage process, which comprises using the reactants aldehyde, cyanide and acid chloride or anhydride in the molar ratio of about 1:(1–1.1):-(1–1.1). It was a surprising fact that this mode of operation gives good to very good yields of the desired products, since according to the state of the art it had to be assumed that the process yields satisfactory results only with partially considerable excess amounts of cyanide (Nowak; Palm, Ohse and Cherdron; cf. above), or—with a smaller cyanide excess—only in the presence of determined phase transfer catalysts (McIntosh, cf. above).

In principle, the process of the invention may be applied to any aldehydes, however, as starting aldehydes there are preferred compounds of the formula I $$R^1 CHO \qquad (I),$$

in which $R^1$ is an optionally substituted $(C_1-C_8)$alkyl (branched or linear),
$(C_3-C_6)$-cycloalkyl,
$(C_2-C_6)$-alkenyl (branched or linear),
$(C_6-C_{10})$-aryl or
benzyl,
preferably
$(C_1-C_4)$-alkyl,
$(C_2-C_3)$-alkenyl,
especially vinyl.

If the groups $R^1$ are substituted, there may be used in principle any substituents that are inert under the conditions of the reaction. In the case of substitution of $R^1$, preferably the alkyl and alkenyl groups are substituted. Preference is given to the following substituents:
Halogen,
$(C_1-C_4)$-alkoxy,
phenyl,
benzyl,
$[(C_1-C_4)$-alkoxy]-carbonyl.

As aldehydes I there may be mentioned by way of example: Acetaldehyde, propional, n-butanal, i-butanal, hexanal, chloroacetaldehyde, diethoxyacetaldehyde, malonic dialdehyde-monodimethyl acetal, succindialdehyde-monodiethyl acetal, glyoxylic acid-methyl ester, cyclohexyl aldehyde, acrolein, methacrolein, ethacrolein, crotonaldehyde, cinnamic aldehyde, benzaldehyde, phenyl acetaldehyde, etc.

As cyanides to be used in the process of the invention there may be mentioned above all alkali metal and ammonium cyanides, especially Na, K and ammonium cyanide. The cyanides have the formula II $$MCN \qquad (II),$$

in whichh M is an alkali metal ion or ammonium ion, preferably a Na, K or $NH_4$ ion.

The cyanides are suitably employed in aqueous solution, as is also the case with the known processes.

As organic acid chlorides and anhydrides there may be used for the process of the invention practically any aliphatic and aromatic acid chlorides and anhydrides, preferably compounds of formula III

(III)

in which $R^2$ is $(C_1-C_4)$-alkyl or phenyl,
preferably $CH_3$ or $C_2H_5$, especially $CH_3$, and $R^3$ is Cl, Br or

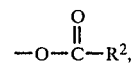

preferably Cl or

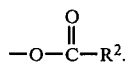

As concrete organic acid chlorides and anhydrides of this kind there may be mentioned by way of example:

Acetyl chloride, propionyl chloride, butyric acid chloride, acetyl bromide, benzoyl chloride, acetic anhydride, propionic acid anhydride, butyric acid anhydride, etc.

Preferred acid chlorides and anhydrides are acetyl chloride an propionyl chloride as well as the corresponding anhydrides, above all acetyl chloride and anhydride.

Like the starting aldehydes, the organic acid chlorides and anhydrides may be used as such or dissolved in an inert organic solvent immiscible with water, for example methylene chloride, carbon tetrachloride, benzene, toluene, ether, etc. An essential feature of the process is the observation of a practically stoichiometrical molar ratio of the aldehyde to the cyanide and acid chloride or anhydride. There are not applied any deviations from the molar ratio of 1:1:1 that are considerably higher than about 10%; they adversely affect especially the economy of the process, in particular with regard to the large amounts of cyanide-containing waste water obtained.

Furthermore, in view of a favorable and economical development of the process, preference is given to the absence of phase transfer catalysts, as they are employed, for example, in the process described by McIntosh (cf. above).

The process of the invention may be carried out both discontinuously and continuously.

The discontinuous operation may in principle be executed in the same manner as has been described in the known pertinent one-stage processes of the state of the art for the manufacture of cyanohydrin acylates of aldehydes, except for the fact that in the present case a different molar ratio of the reactants (about stoichiometrical) is applied and preferably no phase transfer catalysts are used. Thus, for example, the aldehyde may be introduced as such or together with the organic acid chloride or anyhydride, optionally dissolved in an inert organic solvent, and the aqueous cyanide solution may then be added dropwise with cooling. Or, the aqueous cyanide solution is introduced, and the aldehyde and the acid chloride or anhydride, optionally in solution in an inert organic solvent, may be added with cooling, which is a preferred embodiment. It is also possible to introduce all three components in doses about simultaneously into the reaction vessel. As reaction temperatures for the discontinuous operation, those in a range of from about $-20°$ to $+20°$ C., preferably from about $-10°$ to $-+5°$ C. are suitable.

The resulting two-phase reaction mixture is separated into an organic and an aqueous phase, the aqueous phase optionally being extracted with an inert organic solvent, and the extract is worked up (distilled) as usual, together with the organic phase separated before.

However, preference is given to the continuous execution of the process. In this case, all three reactants are continuously fed in doses into the reactor at the same time, and the two-phase reaction solution is continuously drawn off and fed to a phase separator. The organic phase is then worked up as in the case of the discontinuous process. It goes without saying that also with the continuous operation there may be employed simultaneously inert organic solvents, and the aldehyde and the acylating agent, which hardly react with one another at least at non-elevated temperatures, may optionally be pre-mixed. For the continuous operation there may be applied reaction temperatures of from about $-20°$ to $70°$ C., preferably from about $0°$ to $40°$ C.

An inert gas, such as nitrogen or argon, is not required, yet not detrimental, to achieve the reaction. The cyanohydrin acylates are mostly obtained in a liquid form and can therefore be purified by distillation.

If an organic solvent has been used in the reaction, it is recovered during the (distillative) work-up of the reaction mixture and may thus be used again.

Any minor amounts of cyanide possibly present in the waste water obtained in the process can be neutralized by one of the known methods (for example $H_2O_2$ or formalin).

The yields of aldehyde-cyanohydrin acylates obtained by means of the process of the invention are always in the range of from about 80 to 95% of the theory, calculated on the starting aldehyde. If as starting aldehydes there are used compounds of the formula I and as organic acid chlorides or anhydrides compounds of the formula III, the final products have the formula IV

in which $R^1$ and $R^2$ are defined as in formulae I and III.

The novel process represents a considerable improvement owing to its good to very good yield, the simple work-up (distillation of the organic phase without previous neutralization and drying) and high purity of the resulting products, and due to the fact that in consequence of the practically stoichiometrical amounts of the reactants there are hardly left any unconsumed components to be possibly worked up again or eliminated (with the exception of at most minor cyanide amounts which nevertheless may be neutralized in a simple manner). In the case of the continuous operation there is the additional advantage that said operation may be carried out at elevated temperatures, which makes it possible to save the partially considerable expenditure for cooling.

The following Examples illustrate the invention.

EXAMPLE 1

Acetaldehyde-cyanohydrin acetate

400 Grams of 27% aqueous NaCN solution (2.2 mols) and 150 ml of methylene chloride are introduced into a flask. Separately, but simultaneously, 88 g of acetaldehyde (2.0 mols) mixed with 138 ml of methylene chloride and 224 g of acetic anhydride (2.2 mols) mixed with 42 ml of methylene chloride are added dropwise from cooled dropping funnels, with cooling and stirring at $-10°$ C. Upon completion of the dropping and after the addition of 150 ml of water the phases are separated. The organic phase is fractionated first under normal pressure and then in the water jet vacuum. At 20 mbars and $81°$ C., 204.6 g of acetaldehyde-cyanohydrin acetate (90.5% of the theory) are obtained.

EXAMPLE 2

Isobutyraldehyde-cyanohydrin acetate

600 Grams of a 27% aqueous NaCN solution (3.3 mols) are introduced into a flask, and 217 g of isobutyraldehyde (3.0 mols) and 337 g of acetic anhydride (3.3 mols) are added dropwise simultaneously, but separately, within 1 hour at $0°$ to $10°$ C. After the addition of 250 ml of water and separation of the phases, the organic phase is distilled in the water jet vacuum.

Boiling point $_{20\ mbars}$ $78°$ C. Yield: 344.5 g (81.5% of the th.).

EXAMPLES 3 TO 8:
ACROLEIN-CYANOHYDRIN ACETATE

EXAMPLE 3

400 Grams of a 27% aqueous NaCN solution (2.2 mols) are introduced into a flask and cooled to $0°$ C. To this solution are added dropwise within 50 minutes, while stirring, 118 g of 95% acrolein (2.0 mols) and 224.5 g of acetic anhydride (2.2 mols) having been mixed previously. The reaction temperature is maintained at $0°$ C. by external cooling. Upon completion of the dropping, 150 ml of water are added to the reaction mixture to dissolve precipitated inorganic salts. After the product has been separated in the separating funnel, it is distilled in the water jet vacuum. At a boiling point of $73°$ C. at 20 mbars there are obtained 235 g of acrolein-cyanohydrin acetate (94% of the theory).

Purity (gas chromatography): 97.1%.

EXAMPLE 4

814 Grams of 26.5% aqueous NaCN solution (4.4 mols) and 800 g of methylene chloride are introduced into a 4 liter flask and cooled to $0°$ C. 236 Grams of 95% acrolein (4.0 mols) mixed with 180 g of methylene chloride, as well as 449 g of acetic anhydride (4.4 mols) are added dropwise within 30 minutes separately, but simultaneously, with stirring. The internal temperature is maintained at $0°$ C. by external cooling. Upon completion of the dropping, 360 g of water are added to dissolve precipitated salts, and the phases are separated. The lower organic phase is distilled without drying. After elimination of the methylene chloride by distillation under normal pressure, there are obtained 480 g of acrolein-cyanohydrin acetate (96% of the theory), also by distillation, at 20 mbars and $73°$ C.

Purity (gas chromatography): 98%.

EXAMPLE 5

Via ascending tubes 1220 g of 26.5% aqueous NaCN solution (6.6 mols), 354 g of 95% acrolein mixed with 472 g of methylene chloride and 673 g of acetic anhydride (6.6 mols) mixed with 320 g of methylene chloride are introduced dropwise within 1 hour simultaneously, but separately, with stirring, into a 250 ml reactor charged with water and provided with overflow. The internal temperature of the reactor is maintained at $18°$ to $20°$ C. by external cooling. The two-phase reaction solution which is continuously discharged from the reactor is fed to a phase separator, and the lower organic phase is separated and then subjected to distillation. After the elimination of the methylene chloride by distillation under normal pressure, 660 g of acrolein-cyanohydrin acetate (88% of the theory) are distilled at 21 mbars and 74° C.

EXAMPLE 5

The test is carried out as has been described under Example 5, but at a reaction temperature of 30° C.

Yield: 636.6 g of acrolein-cyanohydrin acetate ($\triangleq$84.7% of the th.).

EXAMPLE 6

551 Grams of 26% aqueous KCN solution (2.2 mols) and 350 ml of methylene chloride are introduced into a flask provided with stirrer. To this mixture are added dropwise, within 20 minutes, with stirring and external cooling at −10° C., 118 g of 85% acrolein (2.0 mols) and 157 g of acetyl chloride (2.0 mols) from cooled dropping funnels, simultaneously, but separately. Thereafter 180 ml of water are added and the phases are separated. The aqueous phase is extracted with 100 ml of $CH_2Cl_2$, and the methylene chloride phase is combined with the organic phase previously separated. Upon elimination of the methylene chloride by distillation under normal pressure, a water jet vacuum is applied. There are obtained 214.4 g of acrolein-cyanohydrin acetate (85.5% of the theory).

EXAMPLE 7

90 Milliliters of water and 17 g of a 27% aqueous NaCN solution was introduced into a cooled flask and cooled to 0° C. Thereafter 59 g of 95% acrolein (1 mol) mixed with 105 g (1.03 mols) of acetic anhydride and 170 g of a 27% aqueous NaCN solution (1.03 mols altogether) are added dropwise separately, but simultaneously, at 0° C. with external cooling. Upon completion of the dropping and after the addition of 80 ml of water, the phases are separated and the organic phase is distilled in the water jet vacuum.

Yield: 109.4 g ($\triangleq$87.5% of theory).

EXAMPLE 8

To a two-phase system of 70 g (1.07 mols) of potassium cyanide, 150 ml of water and 300 ml of methylene chloride is added dropwise at −10° C., while stirring vigrously, a mixture pre-cooled to −10° C. of 56 g (1 mol) of acrolein and 110 g (1.08 mols) of acetic anhydride, within about 1 hour. The reaction mixture is allowed to reach room temperature, the organic phase is separated, and the aqueous phase is shaken out twice with methylene chloride. The organic phases are combined and freed from the solvent. Subsequently the residue is distilled under reduced pressure.

115 g (92% of the th.)

Boiling point$_{26\ mbars}$: 82° to 85° C.

EXAMPLE 9

Crotonaldehyde-cyanohydrin acetate

400 Grams of an aqueous 27% NaCN solution (2.2 mols) and 300 ml of methylene chloride are introduced into a flask. While stirring and cooling, 174 g of crotonaldehyde (2.0 mols) in 145 ml of methylene chloride and 224 g of acetic anhydride (2.2 mols) are added dropwise separately, but simultaneously within 35 minutes at about −10° C. After the addition of 150 ml of water and phase separation, the organic phase is distilled first under normal pressure and then in the water jet vacuum. At 25 mbars and 94° C. there are obtained 243 g of crotonaldehyde-cyanohydrin acetate (87.5% of the theory).

EXAMPLE 10

Acrolein-cyanohydrin propionate

200 Grams of an aqueous 27% NaCN solution (1.1 mols) are introduced, together with 100 ml of methylene chloride, into a 1 liter flask and cooled to −15° C. A mixture prepared shortly before of 56 g of acrolein (1.0 mol), 102 g of propionyl chloride (1.1 mols) and 200 ml of methylene chlorids is added dropwise to the above solution within 45 minutes from a cooled dropping funnel, while stirring. The flask contents are maintained at a temperature of from −10° to −15° C. by external cooling. Upon completion of the dropping, 70 ml of water are added and the phases are separated. The organic phase is fractionated first under normal pressure and then in the water jet vacuum. At 25 mbars and 93° to 96° C., 116.1 g of acrolein-cyanohydrin propionate are obtained (83.6% of the theory).

EXAMPLE 11

Methacrolein-cyanohydrin acetate

200 Grams of an aqueous 27% NaCN solution (1.1 mols) are introduced into a 1 liter flask and cooled to 0° C. While stirring, a mixture of 70 g (1 mol) of methacrolein and 112.2 g (1.1 mols) of acetic anhydride is added dropwise within 25 minutes. The flask contents are maintained at 0° C. by external cooling. Upon completion of the addition, the precipitated salts are dissolved by adding 70 ml of water, and the phases are separated. The organic phase is fractionated in the water jet vacuum. At 25 mbars and 90° to 92° C. there are obtained (118.7 g of methacrolein-cyanohydrin acetate (85.5% of the theory).

What is claimed is:

1. A single stage process for the manufacture of a cyanohydrin acylate of an aldehyde which consists of reacting an aldehyde of the formula $R^1$—CHO in which $R^1$ is ($C_1$–$C_8$)-alkyl or ($C_2$–$C_6$)-alkenyl, an aqueous solution of cyanide of the formula MCN in which M is an alkali metal ion or an ammonium ion and an organic acid chloride or acid anhydride of the formula

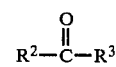

in which $R^2$ is ($C_1$–$C_4$)-alkyl or phenyl and $R^3$ is Cl, Br or

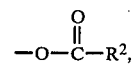

in the presence of an inert organic solvent immiscible in water, in substantially equimolar amounts of 1:(1–1.1):(1–1.1), respectively, at a temperature in the range of −20° C. to +20° C.

2. The process of claim 1 wherein the temperature is in the range of −10° C. to +5° C.

3. The process of claim 1 wherein $R^1$ is ($C_1$–$C_4$)-alkyl.

4. The process of claim 1 wherein $R^1$ is ($C_2$–$C_3$)-alkenyl.

5. The process of claim 1 wherein $R^1$ is vinyl.

6. The process of claim 1 wherein M is Na, K or NH$_4$ ion.

7. The process of claim 1 wherein R$^2$ is methyl.

8. The process of claim 1 wherein R$^2$ is ethyl.

9. A single stage process for the manufacture of a cyanohydrin acylate of an aldehyde which consists of continuously reacting by simultaneously feeding to a reaction vessel an aldehyde of the formula R$^1$—CHO in which R$^1$ is (C$_1$-C$_8$)-alkyl or (C$_2$-C$_6$)-alkenyl, an aqueous solution of cyanide of the formula MCN in which M is an alkali metal ion or an ammonium ion and an organic acid chloride or acid anhydride of the formula

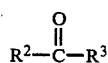

in which R$^2$ is (C$_1$-C$_4$)-alkyl or phenyl and R$^3$ is Cl, Br or

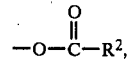

in the presence of an inert organic solvent immiscible in water, in substantially equimolar amounts of 1:(1–1.1):(1–1.1), respectively, at a temperature in the range of −20° C. to +70° C.

10. The process of claim 9 wherein the temperature is in the range of 0° to +40° C.

11. The process of claim 9 wherein R$^1$ is (C$_1$-C$_4$)-alkyl.

12. The process of claim 9 wherein R$^1$ is (C$_2$-C$_3$)-alkenyl.

13. The process of claim 9 wherein R$^1$ is vinyl.

14. The process of claim 9 wherein M is Na, K or NH$_4$ ion.

15. The process of claim 9 wherein R$^2$ is methyl.

16. The process of claim 9 wherein R$^2$ is ethyl.

* * * * *